United States Patent
Bonnet et al.

(10) Patent No.: US 11,364,193 B2
(45) Date of Patent: Jun. 21, 2022

(54) **COSMETIC USE OF A *NEPHELIUM LAPPACEUM* EXTRACT**

(71) Applicant: BASF Beauty Care Solutions France S.A.S., Lyons (FR)

(72) Inventors: Isabelle Bonnet, Lyons (FR); Louis Danoux, Saulxures-lès-Nancy (FR); Charlotte Derceville, Nancy (FR); Solene Mine, Laneuvelotte (FR); Philippe Moser, Dommartemont (FR)

(73) Assignee: BASF Beauty Care Solutions France S.A.S., Lyons (FR)

( * ) Notice: Subject to any disclaimer, the term of this patent is extended or adjusted under 35 U.S.C. 154(b) by 0 days.

(21) Appl. No.: 16/635,951

(22) PCT Filed: Aug. 1, 2018

(86) PCT No.: PCT/FR2018/051972
§ 371 (c)(1),
(2) Date: Jan. 31, 2020

(87) PCT Pub. No.: WO2019/025724
PCT Pub. Date: Feb. 7, 2019

(65) Prior Publication Data
US 2020/0237643 A1    Jul. 30, 2020

(30) Foreign Application Priority Data

Aug. 2, 2017   (FR) ........................................ 1757404
Jan. 16, 2018  (FR) ........................................ 1850351

(51) Int. Cl.
  *A61K 36/00*   (2006.01)
  *A61K 8/9789*  (2017.01)
  *A61Q 19/00*   (2006.01)
  *A61Q 5/00*    (2006.01)

(52) U.S. Cl.
  CPC .............. *A61K 8/9789* (2017.08); *A61Q 5/00* (2013.01); *A61Q 19/00* (2013.01); *A61Q 19/007* (2013.01); *A61K 2236/333* (2013.01)

(58) Field of Classification Search
  CPC ........ A61Q 5/00; A61Q 19/00; A61Q 19/007; A61P 17/00
  See application file for complete search history.

(56) References Cited

U.S. PATENT DOCUMENTS

2004/0037856 A1  2/2004 Catroux et al.
2015/0238462 A1  8/2015 Blanchard et al.

FOREIGN PATENT DOCUMENTS

| CN | 105534812 A   |   | 5/2016  |
|----|---------------|---|---------|
| EP | 3069763 A1    |   | 9/2016  |
| FR | 2940053 A1    |   | 6/2010  |
| FR | 3069450 A1    |   | 2/2019  |
| JP | H04-244004 A  |   | 9/1992  |
| JP | 2002145730 A  |   | 5/2002  |
| KR | 20060007083 A |   | 1/2006  |
| KR | 20090056521 A |   | 6/2009  |
| KR | 101393007 B1  | * | 5/2014  |
| WO | WO-01/87261 A1|   | 11/2001 |
| WO | WO-2011/018278 A2 | | 2/2011 |

OTHER PUBLICATIONS

Sekar et al., 2017, "Formulation and evaluation of novel antiaging cream containing rambutan fruits extract," International Journal for Pharmaceutical Sciences and Research 8(3): 1056-1065.
International Search Report for PCT/FR2018/051972 dated Oct. 2, 2018.
Written Opinion of the International Searching Authority for PCT/FR2018/051972 dated Oct. 2, 2018.
"Eye Cream", Database GNDP Mintel, Accession No. 1349546., XP002782635, Jun. 2010, 6 pages.
Database WPI, Week 200961, Thomson Scientific, London, GB, AN 2009-K31574, XP002779953, Jun. 3, 2009, 1 page.
Search Report for FR Patent Application No. 1757404, dated Apr. 2, 2017, 4 pages.
Search Report for FR Patent Application No. 1850351, dated Jul. 26, 2018, 4 pages.
Search Report for FR Patent Application No. 1901176, dated Aug. 9, 2019, 5 pages.
Suganthi, et al., "*Nephelium lappaceum* (L.): An overview", International Journal of Pharmaceutical Science and Research, vol. 1, Issue 5, Jul. 2016, pp. 36-39.
Thitilertdecha, et al., "Phenolic content and free radical scavenging activities in rambutan during fruit maturation", Scientia Horticulturae, vol. 129, Issue 2, Jun. 10, 2011, pp. 247-252.

\* cited by examiner

*Primary Examiner* — Qiuwen Mi
(74) *Attorney, Agent, or Firm* — Faegre Drinker Biddle & Reath LLP

(57) ABSTRACT

The invention relates to the cosmetic use of a *Nephelium lappaceum* plant extract to reduce the harmful effects of pollution on the skin and/or skin appendages, advantageously the hair, by maintaining and/or increasing the cell viability and/or the ATP synthesis and/or the mitochondrial activity and/or by decreasing the cell senescence and/or the cell damage. The *N. lappaceum* extract increases the radiance of the complexion of the skin.

11 Claims, No Drawings

COSMETIC USE OF A *NEPHELIUM LAPPACEUM* EXTRACT

CROSS-REFERENCE TO RELATED APPLICATIONS

This application is a national stage application (under 35 U.S.C. § 371) of PCT/FR2018/051972, filed Aug. 1, 2018, which claims benefit of French Application No. 1850351, filed Jan. 16, 2018 and French Application No. 1757404, filed Aug. 2, 2017, each of which is incorporated herein by reference in its entirety.

The present invention relates to the cosmetic use of an extract from the *Nephelium lappaceum* plant.

The impact of the environment on human skin is an important issue in the cosmetic and dermatology fields. In addition to the harmful effects of UV on skin, pollutants have a negative impact on both skin and hair. Known pollutants include exhaust gases, which have become a major issue in large cities, heavy metals and fine particles, as well as polycyclic aromatic hydrocarbons such as benzopyrene or benzaanthracene.

In the skin, these pollutants will notably cause particles to be deposited on the surface of the epidermis, and, among other consequences, induce a dull skin complexion. These pollutants also make hair more fragile and lead to hair loss. When they are deposited on the scalp surface, they may also cause itching and irritation. Active ingredients in the cosmetic field already exist to combat pollution. But the need for alternative ingredients in this field is constantly increasing.

The plant *Nephelium lappaceum*, also called rambutan, is a tree found in Southeast Asia, especially Malaysia and Indonesia. It is a tree 10 to 20 meters high, producing a large amount of fruit. The fruit is known for its organoleptic properties and contains sugars, vitamin C and iron. Decoctions of dried roots or leaves have been used to combat fever.

The use of the *N. lappaceum* plant in cosmetic compositions is generally known. Thus, application JP2002145730 describes a seed extract for its antioxidant effect, lightening the skin, as well as for its moisturizing properties. However, this application does not particularly describe or disclose the use of an extract of said plant to reduce the harmful effects of pollution. Moreover, Thitilertdecha and Rakariyatham (Scientia Horticulturae, 129, 247-252, 2011) describe several parts of the *N. lappaceum* plant containing ellagitannins and possessing antioxidant activity. However, this document teaches that it is preferable to use the pericarp rather than another part of said plant since it has a better anti-free radical activity. The same teaching is derived from Sekar et al. (International Journal of Pharmaceutical Sciences and Research. 8(3), 1056-1065, 2017) which shows that it is preferable to use the pericarp of the *N. lappaceum* plant when this plant is to be used as an antioxidant. Sekar et al. furthermore do not disclose that an *N. lappaceum* extract may be used to combat the harmful effects of pollution, i.e., to reduce the unaesthetic and/or uncomfortable effects of pollutants on the skin and/or skin appendages.

Finally, application EP3069763 discloses a cosmetic composition for antioxidant purposes comprising a polyphenolic antioxidant agent. Further, this application does not disclose any *N. lappaceum* extract whatever, nor any of the phenol compounds disclosed in Thitilertdecha and Rakariyatham.

Application CN105534812 discloses a composition having antiinflammatory, antiageing and moisturizing properties for the skin, said composition comprising a mixture of several plant extracts, including rambutan. However, no part of the rambutan plant is disclosed.

Application WO 201118278 discloses the use of a rambutan seed oil for use in a cosmetic composition for hydrating purposes, and more generally for the care of keratin materials, particularly the hair. However, this application does not disclose the use of an *N. lappaceum* extract to combat the harmful effects of pollution on the skin and/or hair.

To the Applicant's knowledge, no prior art either describes or suggests the use of an *N. lappaceum* extract to reduce the harmful effects of pollution on the skin and/or skin appendages, preferentially hair.

The extract according to the invention is an *N. lappaceum* extract. The country of origin of the extract is Vietnam. The Applicant has surprisingly discovered that such an extract has an efficacy for reducing the harmful effects induced by pollution.

The advantage of the extract according to the invention is that it is active for preventing and/or combatting the effects of pollution on both skin and hair. Another advantage of this extract is that it is able to both reduce the effects of pollution by reducing adhesion at the surface of the skin and of the hair, and to increase the cellular metabolism, notably of the hair, by stimulating several targets that help to protect against these pollutants.

It is a chemically-stable extract that does not have allergenic properties and that can be easily produced at the industrial scale. Finally, it is an energizing and depolluting active ingredient for the skin and/or skin appendages, advantageously the hair.

It can both increase the radiance of the complexion of the skin and/or of the skin appendages, advantageously the hair.

A first object of the invention thus concerns the cosmetic use of an extract of the *N. lappaceum* plant to reduce the harmful effects of pollution on the skin and/or skin appendages, advantageously the hair.

The term "cosmetic use" herein is intended to mean a nonpharmaceutical use, which is therefore not for therapeutic purposes, since the extract according to the invention is intended to be applied to all or part of an area of healthy, non-pathological skin. The expression "area of healthy skin" is intended to mean an area of the skin to which the extract according to the invention is applied and which is referred to as "non-pathological" by a dermatologist, that is to say which does not have an infection, scar, skin disease, inflammation or disorder such as candidiasis, impetigo, psoriasis, eczema, acne or dermatitis, or wounds or injuries and/or other dermatoses.

Thus, the skin includes the entire body and/or face, including the scalp.

"Skin appendages" herein is intended to mean body hair, eyelashes, and head hair, and preferentially head hair.

The cosmetic use of the extract according to the present invention may be oral or topical, preferentially topical. When the extract is administered orally, it is in the form of a dietary supplement, powder, gel capsule, capsule or gel. It may therefore be comprised in a nutraceutical composition.

In one embodiment of the invention, the cosmetic use of the extract according to the invention consists of the topical application of the extract or of a cosmetic composition comprising same, to all or part of the human body and/or face, chosen from the legs, feet, underarms, hands, thighs, stomach, chest, neck, arms, torso, back and face, advantageously the face, very advantageously the scalp and/or skin appendages, advantageously the hair.

The extract according to the invention is a topically-acceptable extract, the term "topically-acceptable" meaning an extract that does not irritate the skin or hair, is non-toxic and does not cause an allergic reaction. "Topical application" is intended to mean direct application or spraying of the extract or a cosmetic composition containing same on the surface of the skin and/or skin appendages, preferentially the hair.

In one embodiment of the invention, the extract according to the invention is used to reduce the harmful effects of pollution by maintaining and/or increasing the cell viability and/or the ATP synthesis and/or the mitochondrial activity and/or by reducing the cell damage and/or the cell senescence, advantageously by increasing the cell viability and/or the ATP synthesis and/or the mitochondrial activity, very advantageously by increasing the cell viability and/or the ATP synthesis.

"Reducing the harmful effects of pollution" is intended to mean reducing the unaesthetic and/or uncomfortable effects of pollutants on the skin, advantageously the scalp, and/or skin appendages, advantageously the hair. These effects are distinct from an antioxidant activity. Thus, for the purposes of the invention, the N. lappaceum extract is not used as an antioxidant and/or anti-free radical.

"Unaesthetic and/or uncomfortable effects" is intended to mean herein feelings of irritation and/or redness and/or dullness and/or loss of radiance of the complexion and/or sensitization of the skin and/or skin appendages, that do not require therapeutic treatment, particularly not dermatological treatment. More preferably, they are feelings of irritation and/or redness of the skin, more advantageously of the scalp, and/or skin appendages; and/or feelings of dull complexion and/or loss of radiance of the skin complexion; and/or sensitization of the skin, more advantageously the scalp, and/or skin appendages.

"Pollutants" is intended to mean exhaust gases and/or cigarette smoke and/or dust and/or pollutants, especially coal particles, carbon dioxide, carbon monoxide, sulfur dioxide, nitrogen monoxide, ozone, heavy metals such as cadmium, mercury, nickel, lead, chromium, barium, copper, titanium, fine particles chosen from PM 2.5 and PM 10, as well as polycyclic aromatic hydrocarbons such as benzopyrene or benzaanthracene.

The term "increasing ATP synthesis" herein precisely is intended to mean increasing ATP synthesis by at least 2%, preferentially at least 5%, advantageously at least 15%, preferentially at least 25%, more preferentially at least 40% in fibroblasts of the non-pathological skin, in the presence of the extract according to the invention, in comparison with the ATP level measured in the absence of the extract according to the invention. In one particularly advantageous embodiment of the invention, this increase is measured in the presence of seed extracts prepared according to Example 1a), more advantageously by the enzymatic method under conditions such as described in Example 2a).

In an alternative embodiment of the invention, "increasing ATP synthesis" is intended to mean increasing ATP synthesis by at least 15%, preferentially at least 25%, more preferentially at least 40% in non-pathological hair follicle papilla fibroblasts, in the presence of the extract according to the invention, in comparison with the ATP level measured in the absence of the extract according to the invention. In one particularly advantageous embodiment of the invention, this increase is measured in the presence of the seed extract prepared according to Example 1a), more advantageously by the enzymatic method under conditions such as described in Example 2b).

Increasing mitochondrial activity is intended to mean an increase of at least 15%, preferentially at least 30%, more preferentially at least 40% of said activity in the presence of the extract according to the invention, advantageously measured in normal, i.e., non-pathological, hair papilla fibroblasts, more advantageously in the presence of the seed extract prepared according to Example 1a), in comparison to the level of mitochondrial activity measured in the absence of the extract according to the invention. Preferentially, said activity is measured by optical density after reduction of MTT (3-[4,5-dimethylthiazol-2-yl]-2,5 diphenyltetrazolium bromide) in the presence of succinate dehydrogenase under the conditions described in Example 3.

"Reducing cell senescence" is intended to mean, for the purposes of the invention, a reduction in fibroblast autofluorescence of at least 10%, preferentially at least 20% in the presence of the extract according to the invention, compared with the autofluorescence measured in said fibroblasts without the extract according to the invention. Advantageously, the autofluorescence is measured in hair follicle papilla fibroblasts, more advantageously a neo-papilla model, more preferentially in the presence of the seed extract prepared according to Example 1a). Very advantageously, the autofluorescence is measured by flow cytometry, under the conditions of Example 4.

For the purposes of the invention, "increasing cell viability" is intended to mean an increase in cell viability of at least 5%, advantageously at least 10%, more advantageously at least 20% of the microfollicle cell viability in the presence of the extract according to the invention, in comparison to the level detected without the extract according to the invention. Preferentially, the increase is measured in the presence of the seed extract prepared according to Example 1a), more advantageously by the colorimetric method under the conditions described in Example 6a).

For the purposes of the invention, "decreasing cell damage" is intended to mean decreasing microfollicle cell lysis, advantageously of the hair follicle, by at least 5%, preferentially at least 10%, more preferentially at least 40% in the presence of the extract according to the invention compared to the level of cell lysis measured in the absence of the extract according to the invention. In one advantageous embodiment of the invention, this is a reduction of cell damage measured in the presence of the seed extract prepared according to Example 1a). More advantageously, this decrease is measured by the colorimetric method in the presence of lactate dehydrogenase, under the conditions described in Example 6b). Thus, according to the invention, reducing cell damage does not mean reducing cell oxidation, since the N. lappaceum extract according to the invention is not used as an antioxidant and/or anti-free radical agent.

Alternatively, "reducing cell damage" means reducing damage to the hair fibre by reducing the degradation of one or more of its components chosen from keratin, vitamins, iron, zinc, amino acids, and, advantageously, tryptophan, of at least 2%, advantageously at least 5%, more advantageously at least 10% and very advantageously at least 15%; % of the hair fibre, in the presence of the extract according to the invention, in comparison with said degradation measured in the absence of the extract according to the invention, and preferentially the seed extract prepared according to Example 1a). Advantageously, this reduction is measured by evaluating the tryptophan content of the hair fibre, preferentially the decolorized hair fibre, more preferentially by measuring fluorescence by microscopy and image analysis or by fluorescence spectroscopy or fluorimetry.

In one alternative embodiment of the invention, the extract reduces the harmful effects of pollution by reducing the adhesion and/or the penetration of pollutants, preferentially the adhesion, and preferentially fine particles and/or polycyclic aromatic hydrocarbons, and/or coal particles and/or dust, preferentially polycyclic aromatic hydrocarbons and/or fine particles, in the skin and/or skin appendages, advantageously the hair.

The extract will therefore be present in an effective quantity to reduce the adhesion of pollutants when said percentage is decreased by at least 2%, preferentially at least 5%, more preferentially at least 10% in the presence of the extract according to the invention, in comparison to the percentage of pollutant adhesion measured without the extract according to the invention. In one particularly advantageous embodiment, the extract will be a seed extract, preferentially one prepared under the conditions described in Example 1a). Alternatively, it will be the seed extract prepared according to Example 1h).

Pollutants can be deposited on locks of hair and their effects can be measured, for example, by the use of a so-called pollution chamber, permitting the release of exhaust gases and particles. In one advantageous embodiment of the invention, locks of hair will be exposed to pollutants and the effects thereof will be measured by microscopy and image analysis.

In one particularly advantageous embodiment of the invention, decreasing the adhesion of pollutants in the presence of the *N. lappaceum* seed extract, preferentially the extract according to Example 1a), will be evaluated by measuring the density (μm) of residual pollutant particles on several locks of hair fibres previously treated with the seed extract according to Example 1a).

In one alternative embodiment of the invention, the density (μm) of the residual pollutant particles will be measured on decolorized locks of hair fibres, which are therefore more sensitive to pollutants, previously treated with the seed extract according to the invention, preferentially the seed extract according to Example 1a), or not previously treated.

In one alternative embodiment of the invention, the extract according to the invention reduces the harmful effects of pollution by reducing the cellular autofluorescence increased in the presence of pollutants such as defined for the purposes of the present invention, advantageously benzopyrene. Thus advantageously, the extract according to the invention is in an effective quantity to reduce the cell autofluorescence increased in the presence of benzopyrene when the reduction is at least 35%, preferentially at least 45%, very preferentially at least 70%, in comparison with the level of autofluorescence detected in the presence of benzopyrene. More preferentially, the autofluorescence will be measured in dermal papilla fibroblasts, advantageously in the presence of the seed extract, very advantageously the seed extract prepared under the conditions described in Example 1a), such as described in Example 5.

In yet another alternative embodiment of the invention, the extract reduces the harmful effects of pollution by reducing the cell granularity increased in the presence of pollutants such as defined for the purposes of the present invention, advantageously benzopyrene. Preferentially, the extract according to the invention is in an effective quantity to reduce the cell granularity increased in the presence of benzopyrene when this reduction is at least 30%, preferentially at least 35%, more preferentially at least 40%, in comparison with the level of cell granularity detected in the presence of benzopyrene. Advantageously, this granularity is measured in dermal papilla fibroblasts, advantageously in the presence of the seed extract, very advantageously the seed extract prepared under the conditions described in Example 1a), such as described in Example 5.

In another alternative embodiment of the invention, the extract reduces the harmful effects of pollution by increasing the cell volume decreased in the presence of pollutants, advantageously benzopyrene. Thus, the extract according to the invention is in an effective quantity to increase the cell volume decreased in the presence of benzopyrene when this increase is at least 1%, preferentially at least 2%, in comparison with the cell volume detected in the presence of benzopyrene. Advantageously, this volume is measured in dermal papilla fibroblasts, advantageously in the presence of the seed extract, very advantageously the seed extract prepared under the conditions described in Example 1a).

In yet another alternative embodiment of the invention, the extract reduces the harmful effects of pollution by reducing the cell apoptosis increased in the presence of pollutants such as defined for the purposes of the present invention, advantageously benzopyrene. Preferentially, the extract according to the invention is in an effective quantity to reduce the cell apoptosis increased in the presence of benzopyrene when this reduction is at least 0.5%, preferentially at least 1%, in comparison with the level of cell apoptosis detected in the presence of benzopyrene. Advantageously, this apoptosis is measured in dermal papilla fibroblasts, advantageously in the presence of the seed extract, very advantageously the seed extract prepared under the conditions described in Example 1a).

In yet another alternative embodiment of the invention, the extract reduces the harmful effects of pollution on the skin by increasing, by at least 2%, preferentially at least 5%, more preferentially at least 10%, and very preferentially at least 15%, the total protein content measured in skin fibroblasts cultured in the presence of heavy metals, advantageously mercury and/or cadmium, and in the presence of the extract according to the invention, in comparison to the total protein content measured in the absence of the extract according to the invention. Preferentially, the seed extract prepared under the conditions described in Example 1a).

Advantageously, the total proteins are measured by the Bradford method.

In yet another alternative embodiment of the invention, the extract decreases the harmful effects of pollution on the skin, advantageously the scalp, and/or skin appendages, advantageously the hair, by reducing the expression of heat shock proteins markers, advantageously HSP27, whose expression is increased in the presence of pollutants such as defined according to the present invention, and advantageously cigarette smoke.

The extract according to the invention is therefore used as an energizing and/or depolluting agent for skin and/or skin appendages, advantageously the hair, preferentially depolluting agent. The extract according to the invention makes it possible to increase the radiance of the complexion and/or the homogeneity of the complexion and/or to prevent a loss of radiance and/or homogeneity of the complexion of the skin and/or skin appendages, advantageously the hair.

Particularly, it will be used as a soothing agent for the skin, advantageously the scalp.

In one particularly advantageous embodiment, the extract is used to increase the radiance of the complexion of the skin and/or skin appendages, advantageously the hair, and/or the homogeneity of the complexion and/or prevent a loss of radiance and/or homogeneity of the complexion, by increasing the ATP synthesis.

The increase in the radiance of the complexion and/or the homogeneity of the complexion of the skin and/or skin appendages, preferentially the hair, can be measured in vivo. Thus, in one embodiment of the invention, the term "increasing the radiance of the complexion" of the skin is intended to mean a decrease in dull complexion and/or in yellowing of the skin of at least 1%, preferentially of at least 2%, more preferentially of at least 4%, after application of a cream comprising the extract according to the invention, in comparison with a placebo cream not comprising the extract. Advantageously, this increase in the radiance of the complexion is measured after 15 days, 28 days and/or 56 days, more advantageously on half of the face of a population of women. In one advantageous embodiment of the invention, the increase in the radiance of the complexion is evaluated by measuring the luminescence of the skin, advantageously by measuring the parameter L*. Said parameter can be measured by several techniques chosen from chromometry or image analysis. Advantageously, the parameter L* will be measured by chromometry.

In one alternative embodiment of the invention, the radiance of the complexion is measured by clinical assessment. It may be carried out using an instrument of Goniolux® type or by image analysis. Advantageously, it will be carried out by image analysis.

The extract according to the invention may be all or part of the *N. lappaceum* plant chosen from the bark, leaves, branches, stem, whole fruit, pulp, seeds, pericarp and root. Preferentially, the extract is chosen from among the leaves, pulp, seeds and/or pericarp. Very preferentially, it is a seed extract of the *N. lappaceum* plant.

For the purposes of the invention, "seed extract" is intended to mean any extract of all or part of the *N. lappaceum* plant comprising seeds, advantageously comprising just seeds. Thus, in one preferential embodiment of the invention, the seed extract does not include pericarp or pulp. The seed extract is therefore not a fruit extract. "Pericarp" herein is intended to mean the outer layer of the fruit. The extract can be obtained by various extraction methods known to those skilled in the art, chosen from maceration, hot decoction, by milling including ultrasonic milling, using a mixer, or else the extract can be obtained by extraction in water under subcritical or supercritical conditions (carbon dioxide), Preferentially, the extraction is carried out by maceration.

The extraction may be carried out using dry or fresh matter, advantageously dry matter, in an amount of from 0.1% to 20% by weight, advantageously from 1% to 20%, very advantageously from 5% to 15%, more advantageously from 10% to 15%, even more advantageously of 10% by weight relative to the total weight of the matter and of the extraction solvent.

The extraction may be conducted at a temperature ranging from 4° C. to 300° C. In one preferential embodiment of the invention, the extraction will be carried out at a temperature of from 4° C. to 25° C., more preferentially from 4° C. to 20° C., more advantageously at room temperature, that is to say at approximately 20° C.

In one alternative embodiment of the invention, the extraction will be performed at a temperature of from 60° C. to 90° C. preferentially from 70° C. to 85° C., more preferentially at a temperature of 80° C.

In another alternative embodiment of the invention, the extraction will be carried out in water under subcritical conditions, at a temperature ranging from 100° C. to 300° C., advantageously from 120° C. to 250° C., more advantageously at 120° C. The extraction can be carried out at a single given temperature or at successive increasing temperatures. In one advantageous embodiment of the invention, the extraction will be carried out at a single temperature of 120° C. In an alternative embodiment, it will be carried out according to a gradient of three increasing temperatures of between 100° C. and 200° C., such as 120° C., 140° C. then 160° C., or 110° C., 130° C. then 150° C., or else 120° C., 145° C. then 170° C.

The term extraction under "subcritical conditions" is intended to mean extraction in the presence of water, under conditions of temperature greater than 100° C. and pressure less than 221 bar, such that the water remains in the liquid state but has a viscosity and a surface tension lower than that of water at room temperature, increasing its dielectric constant.

Thus, the extraction pressure will be comprised between 150 bar and 250 bar, preferentially between 200 and 221 bar, advantageously in a pressure extraction autoclave.

In another embodiment of the invention, the extract may be obtained by extraction under supercritical conditions ($CO_2$) in the presence of a cosolvent. Advantageously, the cosolvent will be ethanol.

In yet another alternative embodiment, the extraction will be done in the presence of a $C_6$-$C_{16}$ dialkyl carbonate solvent, such as described in application FR 1757173, incorporated here for reference.

The extraction can be carried out for a period of from 30 minutes to 24 hours, preferentially from 30 minutes to 12 hours, more preferentially for a period of from 1 hour to 5 hours, and more advantageously for a period of from 1 hour to 2 hours. Very advantageously, the extraction will be carried out for a period of 2 hours.

The extract according to the invention may be obtained by extraction in a solvent or solvent mixture, preferably a erotic polar solvent, and advantageously in water, an alcohol, a glycol, a polyol, a water/alcohol, water/glycol or water/polyol mixture (such as water mixed with ethanol, glycerol and/or butylene glycol and/or other glycols such as xylitol and/or propanediol, etc.), from 99/1 to 1/99 (w/w), advantageously in water as sole solvent.

In particular, the extract is obtained by aqueous extraction. For the purpose of the present invention, "extract obtained by aqueous extraction" is intended to mean any extract obtained by extraction with an aqueous solution containing more than 60% by weight, advantageously at least 70% by weight, in particular at least 80% by weight, more particularly at least 90% by weight, particularly at least 95% by weight, of water relative to the total weight of the aqueous solution, even more advantageously not containing glycol and in particular not containing alcohol, more particularly only containing water.

In one particular embodiment, the extract is an *N. lappaceum* seed extract prepared in water as sole solvent.

In an alternative embodiment, the extract is an *N. lappaceum* seed oil extract. In this case, the extract can be particularly be obtained by extraction under supercritical conditions ($CO_2$) or by extraction in a $C_6$-$C_{16}$ dialkyl carbonate solvent or by extraction in heptane.

In another alternative embodiment of the invention, the extraction may be carried out in the presence of a nonionic surfactant, preferentially chosen from lauryl glucoside sold under the name Plantacare® 1200UP by BASF or else caprylyl/capryl glucoside (Plantacare® 810 UP), preferentially capryl/capryl glucoside (Plantacare® 810 UP). The concentration by weight of the nonionic surfactant may be between 0.5% and 5%, advantageously between 0.5 and 1%, more advantageously it will be 1% by weight relative to the total weight of the extract.

Thus, in a first embodiment of the invention, the extract is obtained by maceration of an amount of 10% by weight of milled seeds relative to the weight of solvent and material, for a period of 2 hours at a temperature of 20° C. The crude extract obtained was centrifuged, decanted and then filtered, under the conditions described in Example 1a).

In a second embodiment of the invention, the extract is obtained by maceration of an amount of 5% by weight of milled seeds relative to the total weight of solvent and material, in water as the solvent, at a temperature of 20° C., for a period of 24 hours. The crude extract was centrifuged, decanted and then filtered, under the conditions described in Example 1b).

In a third embodiment of the invention, the extract is obtained by maceration of an amount of 20% by weight of milled seeds in water as solvent, for a period of 2 hours at a temperature of 20° C. The extract is then centrifuged, decanted, filtered and then spray dried in the presence of maltodextrin, in a final amount of maltodextrin of 80% by weight relative to the total weight of the final extract, under the conditions described in Example 1c).

In a fourth embodiment, the extract is obtained by maceration of an amount of 10% by weight of milled seeds relative to the total weight of material and solvent, in a water:ethanol mixture (80:20; v/v), at a temperature of 80° C., for a period of 1 hour. The extract is then centrifuged, decanted, filtered and spray dried in the presence of maltodextrin, in a final amount of maltodextrin of 80% by weight relative to the total weight of the final extract, under the conditions described in Example 1d).

In a fifth embodiment, the extract will be obtained by maceration of an amount of 10% by weight of dried pericarp of *N. lappaceum* relative to the total weight of pericarp and water as sole solvent for a period of 1 hour at a temperature of 20° C. The extract obtained was decanted and centrifuged, then the supernatant was filtered. The extract is in the form of powder, under the conditions described in Example 1e).

In a sixth embodiment, the extraction is done by maceration in water as sole solvent, starting from an amount of 10% by weight of fruit pulp of *N. lappaceum* relative to the total weight of the pulp and water, at a temperature of 80° C. for a period of 1 hour. The crude extract is decanted, centrifuged, then filtered, under the conditions described in Example 1f).

In a seventh embodiment, the extraction is carried out using an amount of 10% by weight of dried leaves of *N. lappaceum* relative to the total weight of the leaves and water, at a temperature of 80° C. for a period of 1 hour. The crude extract is decanted, centrifuged, then filtered, under the conditions described in Example 1g).

In an eighth embodiment, the extraction is carried out using an amount of 10% by weight of dried *N. lappaceum* seeds under the supercritical $CO_2$ conditions described in Example 1h).

In a ninth embodiment, the extraction is carried out using an amount of 5% by weight of dried pericarp relative to the total weight of pericarp and water as sole solvent for a period of 1 hour at a temperature of 20° C. The extract obtained was decanted and centrifuged, then the supernatant was filtered, under the conditions described in Example 1i).

Advantageously according to the invention, the extract will be filtered at a cut-off threshold of 0.45 µm. Additional decolorizing and/or deodorizing steps can be carried out on the extract at any stage of the extraction and according to the techniques known to those skilled in the art. In particular, the extract may be decolorized with activated carbon.

The extract obtained under the conditions described in Examples 1a) and 1b), 1d) to 1i) can then be concentrated by evaporation of the solvent or dried for example by freeze-drying or by spray-drying in the presence of maltodextrins. The extract will then be in powder form.

Thus, in one particular embodiment of the invention, the extract obtained according to Examples 1a) and 1b), 1d) to 1i) will be spray-dried in the presence of a concentration by weight of maltodextrins of between 20% and 90%, preferentially between 40% and 80%, more preferentially from 70% to 80% relative to the total weight of the powder obtained.

Thus, in one particularly advantageous embodiment of the invention, the use of the extract reduces the harmful effects of pollution on the skin, advantageously the scalp and/or skin appendages, advantageously the hair, by increasing the cell viability and/or the ATP synthesis and/or the mitochondrial activity and/or by decreasing the cell damage and/or the cell senescence, more preferentially by increasing the ATP synthesis. Preferentially in this case, the extract is a leaf, seed, pericarp and/or pulp extract, more preferentially a seed extract.

The extract according to the invention may be used alone in the form of a cosmetic active ingredient, or be comprised in a cosmetic composition.

When it is used alone in the form of a cosmetic ingredient, it is preferentially solubilized in an aqueous solution containing glycerin, advantageously present at a concentration of from 60% to 90%, more advantageously from 70% to 85%, very advantageously at a concentration of 80% by weight relative to the total weight of the aqueous solution comprising the extract. The extract is then in liquid form.

In one alternative embodiment of the invention, the extract will be solubilized and/or diluted in a solvent, in particular a polar solvent, such as water, an alcohol, a polyol, a glycol, such as pentylene glycol and/or butylene glycol and/or hexylene glycol and/or caprylyl glycol, or a mixture thereof, preferentially an aqueous-glycolic mixture, more preferentially containing a glycol chosen from hexylene glycol, caprylyl glycol and mixtures thereof. Advantageously, the extract obtained is diluted and/or soluble in an aqueous solution containing hexylene glycol, in particular containing between 0.1% and 10% by weight of hexylene glycol, preferentially between 0.5% and 5% by weight of hexylene glycol, relative to the total weight of the cosmetic ingredient. Advantageously, the extract obtained is diluted and/or soluble in an aqueous solution containing caprylyl glycol, in particular containing between 0.01% and 5% by weight of caprylyl glycol, preferentially between 0.1% and 1% by weight of caprylyl glycol, relative to the total weight of the aqueous solution comprising the extract.

In particular, the aqueous solution in which the *N. lappaceum* extract is solubilized according to the invention comprises xanthan gum, in particular between 0.01% and 5% by weight of xanthan gum, relative to the total weight of the aqueous solution, more particularly between 0.1% and 1% by weight of xanthan gum relative to the total weight of the aqueous solution comprising the extract.

Advantageously, the solution in which the *N. lappaceum* extract is solubilized according to the invention comprises hexylene glycol, caprylyl glycol and xanthan gum.

Another subject of the invention therefore concerns the use of the extract according to the invention, in a cosmetic composition comprising at least one cosmetically-acceptable excipient, to reduce the harmful effects of pollution on the skin, advantageously the scalp, and/or skin appendages, advantageously the hair. The term "acceptable" is intended to mean a cosmetic excipient or excipient non-irritating to the skin, which does not induce an allergic response and is chemically stable.

Thus, the cosmetic composition is used to reduce the harmful effects of pollution on the skin and/or skin appendages, advantageously the hair.

The cosmetic composition comprising the extract according to the invention, preferentially a leaf, pericarp, pulp and/or seed extract, very preferentially a seed extract, can be used as an energizing and/or depolluting cosmetic composition, advantageously depolluting, more advantageously for the hair.

The composition can be administered topically or orally. In one advantageous embodiment of the invention, said cosmetic composition will be applied topically, advantageously to all or part of the human body chosen from the legs, feet, underarms, hands, thighs, stomach, chest, neck, arms, torso, back and face, advantageously the face, very advantageously the scalp and/or skin appendages, advantageously the hair.

In one embodiment of the invention, the extract according to the invention will be present in the cosmetic composition at a concentration of $1 \times 10^{-4}$% to 10%, preferentially from $1 \times 10^{-4}$% to 5%, and more preferentially from $1 \times 10^{-3}$% to 3% by weight, relative to the total weight of the composition.

The excipient(s) may be chosen from surfactants and/or emulsifiers, preservatives, buffers, chelating agents, denaturing agents, opacifiers, pH adjusters, reducing agents, stabilizers, thickeners, gelling agents, film-forming polymers, fillers, mattifying agents, gloss agents, pigments, dyes, fragrances and mixtures thereof. The CTFA (Cosmetic Ingredient Handbook, Second Edition (1992)) describes various cosmetic excipients suitable for use in the present invention.

Advantageously, the excipient(s) are chosen from the group comprising polyglycerols, esters, cellulose polymers and derivatives, lanolin derivatives, phospholipids, lactoferrins, lactoperoxidases, sucrose-based stabilizers, vitamin E and its derivatives, xanthan gums, natural and synthetic waxes, vegetable oils, triglycerides, unsaponifiables, phytosterols, silicones, protein hydrolysates, betaines, aminoxides, plant extracts, saccharose esters, titanium dioxides, glycines, and parabens, and more preferably from the group consisting of steareth-2, steareth-21, glycol-15 stearyl ether, cetearyl alcohol, phenoxyethanol, methylparaben, ethylparaben, propylparaben, butylparaben, butylene glycol, caprylyl glycol, natural tocopherols, glycerin, dihydroxycetyl sodium phosphate, isopropyl hydroxyketyl ether, glycol stearate, triisononanoine, octyl cocoate, polyacrylamide, isoparaffin, laureth-7, a carbomer, propylene glycol hexylene glycol, glycerol, bisabolol, dimethicone, sodium hydroxide, PEG 30-dipolyhydroxysterate, capric/caprylic triglycerides, cetearyl octanoate, dibutyl adipate, grape seed oil, jojoba oil, magnesium sulfate, EDTA, a cyclomethicone, xanthan gum, citric acid, sodium lauryl sulfate, waxes and mineral oils, isostearyl isostearate, propylene glycol dipelargonate, propylene glycol isostearate, PEG 8, beeswax, glycerides of hydrogenated palm heart oil, lanolin oil, sesame oil, cetyl lactate, lanolin alcohol, castor oil, titanium dioxide, lactose, saccharose, low density polyethylene, an isotonic saline solution, and mixtures thereof.

The cosmetic composition may be chosen from an aqueous or oily solution, a cream or an aqueous gel or an oily gel, especially a shower gel, a milk, an emulsion, a microemulsion or a nanoemulsion, which is especially oil-in-water or water-in-oil or multiple or silicone-based, a mask, a serum, a lotion, a liquid soap, a dermatological bar, an ointment, a foam, a patch, an anhydrous product, which is preferably liquid, pasty or solid, a shampoo. Advantageously, it is a shampoo.

The cosmetic composition may also comprise other cosmetic agents having the same properties and possibly inducing a synergistic effect with the extract according to the invention, or cosmetic agents with complementary effects.

Cosmetic agents known for their use to protect skin from the penetration of toxic molecules, or use as detoxifying agents, or depolluting agents notably include a *Caesalpinia spinosa* extract and hydrolysed extracts of *Chondrus crispus* or *Kappaphycus striatum*. An argan oil extract sold under the name Arganyl™ or a seed extract of *Moringa oleifera* sold under the names of Purisoft™ and Puricare™ by the applicant can also be mentioned.

Other types of active agents may be present in the composition, such as anti-aging ingredients and/or bleaching active agents, antipollution ingredients and/or ingredients which promote the radiance of the complexion.

These may for example be a leaf extract of *Cassia alata* sold under the name DN-Age™ and/or an extract of lychees sold under the name Litchiderm™ as antioxidant active agents, a combination of an extract of *Salvia miltiorhizza* and of niacinamide, sold under the name CollRepair™ as a deglycating agent, an antiwrinkle extract of chicory, sold under the name Lox-Age™, an extract of *Achiliea millefolium* sold under the name Neurobiox™, an extract of *Polygonum bistoria* sold under the name Perlaura™, an extract of galanga sold under the name Hyalufix™, an extract of corn sold under the name Deliner™ or an extract of *Voandzeia subterranea* sold under the name Epigenist™ by the applicant or else active agents which promote the firmness of the skin, such as a synthetic tetrapeptide sold under the name Dermican™, an extract of *Hibiscus abelmoschus* sold under the name Linefactor™, a purified extract of pea sold under the name Proteasyl™, an extract of *Manilkara multinervis* sold under the name Elestan™ a pulp extract of Argan sold under the name Argassential™ by the applicant. An extract of the *Origanum majorana* plant sold under the name Dermagenist™ and/or an extract of *Khaya senegalensis* sold under the name Collalift™ 18 may also be added to the cosmetic composition.

Yet another object of the present invention is a cosmetic care method comprising the topical or oral administration of the extract according to the invention or a cosmetic composition containing same to increase the cell viability and/or the ATP synthesis and/or the mitochondrial activity and/or to decrease the cell damage and/or to decrease the cell senescence, and/or to decrease the harmful effects of pollution on the skin, advantageously the scalp and/or the skin appendages, advantageously the hair. Preferentially, the administration is a topical application. In one embodiment of the invention, the cosmetic care method consists of the topical application of the extract according to the invention or a composition comprising same, to all or part of the human body, chosen from the legs, feet, underarms, hands, thighs, stomach, chest, neck, arms, torso, back and face, advantageously the face, very advantageously the scalp and/or skin appendages, advantageously the hair.

The examples refer to the description of the invention and are presented below. These examples are given for illustrative purposes and do not limit the scope of the invention in any way. Each of the examples has a general scope. The examples are an integral part of the present invention, and any feature appearing to be novel over any prior art whatsoever, from the description taken in its entirety, including the examples, is an integral part of the invention.

Finally, unless otherwise specified, in the examples, the temperature is expressed in degrees Celsius, the percentages by weight per volume, and the pressure is the atmospheric pressure.

EXAMPLE 1

Methods for Preparing an Extract of *N. lappaceum* According to the Invention

Example 1a)

An amount of 10% by weight of milled seeds of *N. lappaceum* relative to the total weight of solvent and seeds was obtained by maceration in water as solvent, at a temperature of 20° C. for a period of 2 hours. The crude extract was centrifuged, decanted and then filtered.

Example 1b)

An amount of 5% by weight of milled seeds of *N. lappaceum* relative to the total weight of solvent and seeds was obtained by maceration in water as solvent, at a temperature of 20° C. for a period of 24 hours. The crude extract was centrifuged, decanted and then filtered.

Example 1c)

An amount of 20% by weight of milled seeds of *N. lappaceum* relative to the total weight of solvent and seeds was obtained by maceration in water as solvent, at a temperature of 20° C. for a period of 2 hours. The crude extract was centrifuged, decanted and then filtered. The extract was spray-dried in the presence of maltodextrin, in a final maltodextrin amount of 80% by weight relative to the total weight of the final extract.

Example 1d)

An amount of 10% by weight of milled seeds of *N. lappaceum* relative to the total weight of solvent and seeds was extracted by maceration in an ethanol:water mixture (80:20 v/v) as solvent, at a temperature of 80° C. for a period of 1 hour. The crude extract was centrifuged, decanted and then filtered. The extract was spray-dried in the presence of maltodextrin, in a final maltodextrin amount of 80% by weight relative to the total weight of the final extract.

Example 1e)

An amount of 10% by weight of dried pericarp of *N. lappaceum* relative to the total weight of pericarp and water as sole solvent was extracted by maceration for a period of 1 hour at a temperature of 80° C. The extract obtained was decanted and centrifuged, then the supernatant was filtered. The extract is in powder form.

Example 1f)

The extraction was carried out by maceration in water as sole solvent, starting from an amount of 10% by weight of fruit pulp of *N. lappaceum* relative to the total weight of the pulp and water, at a temperature of 80° C. for a period of 1 hour. The crude extract was decanted, centrifuged and then filtered.

Example 1g)

An amount of 10% by weight of dried leaves of *N. lappaceum* relative to the total weight of leaves and water as sole solvent was extracted by maceration for a period of 1 hour at a temperature of 20° C. The extract obtained was decanted and centrifuged, then the supernatant was filtered. The extract is in powder form.

Example 1h)

An amount of 10% of dried seeds was obtained by extraction under supercritical $CO_2$ conditions, in the presence of ethanol as cosolvent (10%).

Example 1i)

An amount of 5% by weight of dried pericarp relative to the total weight of pericarp and water as sole solvent was extracted by maceration for a period of 1 hour at a temperature of 20° C. The extract obtained was decanted and centrifuged, then the supernatant was filtered. The extract is in liquid form.

EXAMPLE 2

Demonstration of the Increase in ATP Synthesis in the Presence of an *N. lappaceum* Extract Example 2a)

ATP Synthesis in Skin Fibroblasts

Protocol: Normal, that is to say non-pathological, human fibroblasts were incubated for 6 days at 37° C. ($CO_2$=5%, 95% relative humidity) on a growth medium comprising DMEM and 10% of fetal calf serum. The medium was replaced by a Hanks saline solution with or without the extract according to the invention (Control). After an incubation period of 24 hours, the cells were irradiated under UVA and then returned to culture for a period of 24 hours, at 37° C.

Cell ATP was extracted with DMSO and assayed on an extract aliquot by enzymatic method (Luciferin/Luciferase Complex; ATP Bioluminescence kit ROCHE Diagnostics).

Results (SD: Standard deviation):

TABLE 1

| | MEAN | SD |
|---|---|---|
| Control | 100 | 7 |
| Seed extract of *N. lappaceum* Ex. 1a) 1% (v/v) | 139 | 3 |
| Pericarp extract of *N. lappaceum* Ex. 1e) 0.1% (v/v) | 108 | 7 |
| Pulp extract of *N. lappaceum* Ex. 1f) 0.5% (v/v) | 107 | 5 |
| Leaf extract of *N. lappaceum* Ex. 1g) 1% (v/v) | 105 | 2 |

Conclusion: the pulp, seed, leaf and pericarp extracts showed an increase in ATP synthesis by comparison to the control, by having an energizing and depolluting action for the skin.

Example 2b)

ATP Synthesis in Hair Follicle Papilla Fibroblasts

Protocol: Non-pathological human fibroblasts from hair follicle papilla were cultured in DMEM medium for 24 hours and then treated for 6 days with *N. lappaceum* aqueous seed extract according to the invention, at final concentrations by volume of 0.03% and 0.01% relative to the total volume of the medium. The same medium was cultured in the absence of extract according to the invention (Control). The amount of ATP was measured at the end of 6 days by the enzymatic method (Lnciferin/Luciferase Complex; ATP Bioluminescence kit ROCHE Diagnostics).

TABLE 2

|  | MEAN | SD |
|---|---|---|
| Control | 100 | 7 |
| Seed extract of N. lappaceum Ex. 1a) 0.03% (v/v) | 138 | 6 |
| Seed extract of N. lappaceum Ex. 1a) 0.1% (v/v) | 139 | 3 |

Conclusion: the seed extracts showed an increase in ATP synthesis in comparison to the control. Consequently, the seed extract has an energizing and depolluting action on the scalp and/or skin appendages, preferentially the hair, and therefore makes it possible to increase the radiance of the complexion and/or the homogeneity of the complexion and/or to prevent loss of radiance and/or homogeneity of the complexion.

EXAMPLE 3

Demonstration of the Increase in Mitochondrial Metabolic Activity of Hair Papilla Fibroblasts by the Extract According to the Invention Protocol: Non-pathological human hair follicle papilla fibroblasts were cultured for 24 hours and then treated for 6 days with N. lappaceum aqueous seed extract at final concentrations by volume of 0.1% and 0.3% relative to the total volume of the medium. The same medium was cultured in the absence of extract according to the invention (Control). Fibroblast mitochondrial activity was measured by MTT (3-[4,5-dimethylthiazol-2-yl]-2,5 diphenyltetrazolium bromide) reduction in the presence of succinate dehydrogenase. The precipitate obtained was extracted with DMSO, and then the optical density of the DMSO solution was measured at 540 nm.
Results:

TABLE 3

|  | MEAN | SD |
|---|---|---|
| Control | 100 | 2 |
| Seed extract of N. lappaceum Ex. 1a) 0.1% (v/v) | 121 | 4 |
| Seed extract of N. lappaceum Ex. 1a) 0.3% (v/v) | 145 | 4 |

Conclusion: the N. lappaceum aqueous seed extract showed an increase of mitochondrial activity of hair follicle papilla fibroblasts of at least 15% in comparison with the control, up to 47%. This mitochondrial activity participates in the reduction of the harmful effects induced by pollution on the scalp and/or skin appendages, preferentially the hair and increases the radiance of the complexion and/or the homogeneity of the complexion and/or prevents loss of radiance and/or homogeneity of the complexion.

EXAMPLE 4

Reduction of Autofluorescence Parameters in a Neo-Papilla Cell Model

Protocol: Normal, non-pathological human fibroblasts were suspended in DMEM medium comprising the seed extract according to the invention prepared according to Example 1a) at the final concentration by volume of 1% relative to the total volume of the medium. The same medium was cultured in the absence of extract according to the invention (Control). After centrifugation, the aggregates were incubated for 5 days at 37° C. (5% $CO_2$). The aggregates were rinsed in PBS butler then the cells were lysed in a protease mixture with EDTA.

Cell autofluorescence was determined using a C6 flow cytometer (Becton-Dickinson UK) (585 nm+/−20 nm). The results are expressed as % relative to the control.
Results:

TABLE 4

|  | MEAN | SD |
|---|---|---|
| Control | 100 | 8 |
| Seed extract of N. lappaceum Ex. 1a) 1% (v/v) | 74 | 2 |

Conclusion: the seed extract demonstrated its ability to reduce the fibroblast autofluorescence by at least 20%, therefore reducing the fibroblast senescence in the hair follicle papilla.

EXAMPLE 5

Protective Effect of the Extract According to the Invention Against a Pollutant, Benzopyrene Protocol: A suspension of non-pathological human dermal papilla fibroblasts was prepared by culture of said fibroblasts in a basal culture medium in the presence of a growth factor solution (0.2% v/v), to which benzopyrene (BaP) was added at final concentrations of 5 or 10 µmol/L final medium, therefore a final concentration of 0.5% (w/v medium) of N. lappaceum seed extract prepared according to Example 1a) or without extract (Control) The suspension was centrifuged (5 min, 200 g) then the aggregates obtained were incubated at 37° C. (5% $CO_2$) for a period of 5 days.

For the analysis of cell autofluorescence (Table 5) and cell granularity (Table 6), the aggregates were recovered after 5 days of incubation, rinsed with phosphate buffer saline (PBS) buffer then dislocated by incubation in a mixture of proteases and EDTA for one hour at a temperature of 37° C. The cell suspension obtained was then analyzed by flow cytometry. Autofluorescence was measured at 585 nm. An increase in cell autofluorescence and cell granularity are characteristic of fibroblast degradation and demonstrates an effect of the pollutant analyzed.

Cell autofluorescence results (n=2):

TABLE 5

|  | Cell autofluorescence | |
|---|---|---|
|  | MEAN | SD |
| Control | 100 | 0 |
| BaP (5 µmol/L medium) | 212 | 21 |
| BaP (5 µmol/L milieu) + N. lappaceum seed extract from Example 1a) at 0.5% (w/v final medium) | 150 | 6 |

Conclusion: Benzopyrene increased the degree of autofluorescence by at least 191% in fibroblasts. In return, the addition of the N. lappaceum seed extract in the presence of the pollutant counterbalanced this degradation by reducing the extent of autofluorescence detected in the presence of benzopyrene alone by at least 35%, demonstrating that the extract is effective for combatting cell degradation induced by benzopyrene.

Cell granularity results (n=3):

TABLE 6

|  | MEAN | SD |
|---|---|---|
| Control | 100 | 0 |
| BaP (5 μmol/L medium) | 113 | 4 |
| BaP (5 μmol/L milieu) + N. lappaceum seed extract from Example 1a) at 0.5% (w/v final medium) | 76 | 2 |

Conclusion: the addition of benzopyrene into the medium increased the particle size of aggregates by at least 9%. In return, the concomitant addition of *N. lappaceum* seed extract reduced the particle size detected in the presence of the pollutant by at least 31%, demonstrating that the extract is effective for combatting cell degradation induced by benzopyrene.

EXAMPLE 6

Demonstration of the Effect of the Extract According to the Invention on Micro-Follicles Method for Reconstructing a Micro-Follicle:

The micro-follicle model consists of 3D co-culturing of papilla fibroblasts, keratinocytes from the outer sheath of the hair follicle and melanocytes. This cell model is the reconstructed organ molecule closest to the hair follicle by allowing the integration of neural, epidermal and mesenchymatous interactions among the different types of cells. The micro-follicles were cultured. Non-pathological papilla fibroblasts were cultured for 3 days. Melanocytes and keratinocytes from the outer sheath of the hair follicle were then added to the neo-papilla to form the micro-follicle. After 24 h of culture, the *N. lappaceum* aqueous seed extract was added. The same medium was cultured without extract according to the invention (Control). The culture media and micro-follicles were sampled after 48 h of treatment for testing.

Example 6a)

Increase in Cell Viability in Micro-Follicles

Protocol:

Micro-follicle cell viability was measured by the Presto-Blue (Thermo Fisher Scientific) method. This colorimetric method is based on the reduction and fluorescence emission of a resazurin reagent by viable cells. The measurements were done after 48 h of treatment. The values are expressed in mean % after normalization by the untreated control.

Result:

TABLE 7

|  | MEAN | SD |
|---|---|---|
| Control | 100 | 6.7 |
| Seed extract of *N. lappaceum* Ex. 1a) 0.02% (v/v) | 118.0 | 6.5 |

Conclusion: the seed extract according to the invention is able to increase micro-follicle cell viability, therefore it is an active extract to reduce stress induced by pollution, especially of the scalp and/or skin appendages, preferentially the hair.

Example 6b)

Reduction of Cell Damage in the Micro-Follicle

Protocol: Cell damage was measured by the colorimetric method in the presence of lactate dehydrogenase, allowing quantification of the cytotoxicity of an extract on the measurement of the lactate dehydrogenase activity in damaged cells in the culture medium. An increase in cell membrane damage and cell lysis leads to an increase in lactate dehydrogenase activity proportional to the number of lysed cells. The activity is demonstrated in the presence of formazan, the amount of which was assessed by measuring optical density (500 nm). Measurements were conducted in culture medium after 48 h of treatment in the presence of a final concentration of extract according to the invention by volume of 0.02% relative to the total volume of the medium, or without extract (Control).

Result:

TABLE 8

|  | MEAN | SD |
|---|---|---|
| Control | 100 | 15.9 |
| Seed extract of *N. lappaceum* Ex. 1a) 0.02% (v/v) | 58.0 | 16.3 |

Conclusion: the seed extract according to the invention is able to reduce the cell damage, by creating an active extract to reduce the harmful effects of pollution, especially on the scalp and skin appendages, preferentially the hair.

EXAMPLE 7

Example of Cosmetic Ingredient Comprising the *N. lappaceum* Extract

| *N. lappaceum* seed extract (Ex. 1c) | 20% by total weight |
|---|---|
| Maltodextrins | 80% by total weight |

EXAMPLE 8

Examples of Cosmetic Compositions Comprising the Extract According to the Invention The compositions below are prepared according to methods known to those skilled in the art, in particular as regards the various phases to be mixed together. The amounts indicated are as percentage by weight relative to the total weight of the composition.

Example 8a)

Body and Face Serum

| Phase | Name | Amount (% by total weight) |
|---|---|---|
| A | Water | 94.75 |
| A | Preservative | qs 100 |

-continued

| Phase | Name | Amount (% by total weight) |
|---|---|---|
| A | Glycerine | 1.00 |
| B | Xanthan gum | 0.2 |
| B | Sodium polyacrylate | 0.25 |
| C | Cosmetic ingredient according to Example 7 | 1-5 |

Example 8b)

Face Cream

| | |
|---|---|
| Cosmetic ingredient according to Example 7 | 1.00-10% |
| Xanthan gum | 0.50 |
| EDTA | 0.05 |
| Steareth-2 | 2.00 |
| Steareth-21 | 2.50 |
| Cetearyl alcohol | 1.00 |
| Propylheptyl caprylate | 15.00 |
| Sodium hydroxide (30% in solution) | 0.10 |
| Mixture of phenoxyethanol, chlorphenesin, benzoic acid, butylene glycol, sorbic acid (Germazide ™ PBS) | 1.25 |
| Mixture of polyacrylate-X, isohexadecane and polysorbate 60 (Sepigel ™ SMS 60) | 4.00 |
| Water | qs 100 |

The invention claimed is:

1. A cosmetic care method comprising administering topically or orally a *Nephelium lappaceum* seed extract, or a cosmetic composition comprising the seed extract, to a human to reduce the harmful effects of pollution on the skin, the scalp, the hair, and/or skin appendages, wherein the extract is obtained by extraction of *Nephelium lappaceum* seeds at approximately 20° C. for 1 to 5 hours in water as sole solvent.

2. The cosmetic care method as claimed in claim 1, wherein the extract reduces the unaesthetic and/or uncomfortable manifestations of pollutants on the skin, the scalp, the hair, and/or skin appendages.

3. The cosmetic care method as claimed in claim 1, wherein the extract reduces the feelings of irritation and/or redness of the skin and/or skin appendages, and/or dull complexion and/or loss of radiance of the complexion of the skin, and/or sensitization of the skin and/or skin appendages.

4. The cosmetic care method as claimed in claim 1, wherein the extract increases the cell viability and/or the ATP synthesis and/or the mitochondrial activity and/or decreases the cell senescence and/or the cell damage.

5. The cosmetic care method as claimed in claim 1, wherein the extract is administered topically.

6. The cosmetic care method as claimed in claim 1, wherein the extract is present in a cosmetic composition comprising at least one cosmetically-acceptable excipient, and wherein the extract is present in the cosmetic composition at a final concentration of $1\times10^{-4}$% to 10% by weight, relative to the total weight of the cosmetic composition.

7. The cosmetic care method as claimed in claim 1, wherein the extract is an energizing and/or depolluting agent for skin and/or skin appendages and/or the hair.

8. The cosmetic care method as claimed in claim 6, wherein the cosmetic composition is in a form selected from the group consisting of an aqueous solution, oily solution, a cream, an aqueous gel, an oily gel, a shower gel, a milk, an emulsion, a microemulsion, a nanoemulsion, a mask, a serum, a lotion, a liquid soap, a dermatological bar, an ointment, a foam, a patch, an anhydrous product, and a shampoo.

9. The cosmetic care method as claimed in claim 5, wherein the extract or the cosmetic composition is administered topically to all or part of the human body selected from the group consisting of legs, feet, underarms, hands, thighs, stomach, chest, neck, arms, torso, back and face, the scalp and/or skin appendages, and the hair.

10. The cosmetic care method as claimed in claim 6, wherein the extract is present in the cosmetic composition at a final concentration of $1\times10^{-3}$% to 3% by weight, relative to the total weight of the cosmetic composition.

11. The cosmetic care method as claimed in claim 1, wherein the *Nephelium lappaceum* seed extract is obtained by extraction at approximately 20° C. for 1 to 2 hours in water as sole solvent.

* * * * *